(12) United States Patent
Archer

(10) Patent No.: US 9,669,010 B2
(45) Date of Patent: Jun. 6, 2017

(54) TREATMENT FOR CHRONIC KIDNEY DISEASE

(71) Applicant: Bio Health Solutions, LLC, Reno, NV (US)

(72) Inventor: James Archer, Los Angeles, CA (US)

(73) Assignee: Bio Health Solutions, LLC, Reno, NV (US)

(*) Notice: Subject to any disclaimer, the term of this patent is extended or adjusted under 35 U.S.C. 154(b) by 0 days.

(21) Appl. No.: 14/649,547

(22) PCT Filed: Dec. 6, 2013

(86) PCT No.: PCT/US2013/073732
§ 371 (c)(1),
(2) Date: Jun. 3, 2015

(87) PCT Pub. No.: WO2014/089526
PCT Pub. Date: Jun. 12, 2014

(65) Prior Publication Data
US 2015/0297567 A1 Oct. 22, 2015

Related U.S. Application Data

(63) Continuation-in-part of application No. 13/892,225, filed on May 10, 2013, now abandoned.

(60) Provisional application No. 61/734,080, filed on Dec. 6, 2012.

(51) Int. Cl.
| A61K 9/00 | (2006.01) |
| A61K 31/00 | (2006.01) |
| A61K 31/4172 | (2006.01) |
| A61K 31/198 | (2006.01) |
| A61K 9/14 | (2006.01) |

(52) U.S. Cl.
CPC ........ *A61K 31/4172* (2013.01); *A61K 9/0053* (2013.01); *A61K 9/14* (2013.01); *A61K 31/198* (2013.01)

(58) Field of Classification Search
CPC ............ A61K 2300/00; A61K 31/4172; A61K 31/198; A61K 9/14; A61K 9/0053
See application file for complete search history.

(56) References Cited

U.S. PATENT DOCUMENTS

| 5,036,052 A | * | 7/1991 | Ozeki | A23L 1/3051 |
| | | | | 514/400 |
| 6,060,446 A | * | 5/2000 | Zaloga | A23L 1/305 |
| | | | | 426/648 |
| 6,358,530 B1 | * | 3/2002 | Eljamal | A61K 9/0075 |
| | | | | 424/488 |
| 6,403,144 B1 | * | 6/2002 | El-Khoury | A23D 7/0053 |
| | | | | 106/2 |
| 8,685,481 B2 | * | 4/2014 | Dubbelman | A23L 1/2128 |
| | | | | 426/489 |
| 2002/0058070 A1 | * | 5/2002 | Felisaz | A61K 9/2013 |
| | | | | 424/489 |
| 2004/0247560 A1 | | 12/2004 | Dirk et al. | |
| 2007/0286909 A1 | | 12/2007 | Smith et al. | |
| 2008/0269117 A1 | * | 10/2008 | Hageman | A23L 1/296 |
| | | | | 514/1.1 |
| 2012/0270791 A1 | * | 10/2012 | Leamon | A61K 47/48107 |
| | | | | 514/15.4 |
| 2013/0065822 A1 | * | 3/2013 | Miller | A23C 11/04 |
| | | | | 514/5.6 |
| 2014/0127227 A1 | * | 5/2014 | Chang | A61K 47/183 |
| | | | | 424/158.1 |
| 2015/0230488 A1 | * | 8/2015 | de Man | A23D 9/007 |
| | | | | 426/603 |

FOREIGN PATENT DOCUMENTS

| DE | WO 2009033755 A2 | * | 3/2009 | ............ A61K 38/08 |
| JP | EP 0347890 A1 | * | 12/1989 | ............ A23L 1/3051 |
| RU | 2077883 C1 | | 4/1997 | |
| WO | 95/29675 A1 | | 9/1995 | |
| WO | 98/18467 A1 | | 5/1998 | |
| WO | 2007/026474 A1 | | 8/2007 | |

OTHER PUBLICATIONS

Archer, "Effect of AB070597 on Blood-Serum Creatinine Concentration in Cats with Chronic Kidney Disease," Research Journal for Veterinary Practitioners, 2015, 3(3):58-68.
Balzola et al, "The metabolic role of glutamine", (1996) Minerva Gastroenterol. Dietol. 42(1): 17-26 [Abstract Only].
Bergstrom et al., "Intracellular free amino acids in muscle tissue of patients with chronic uremia: effect of peritoneal dialysis and infusion of essential amino acids", (1978) Clin. Sci. Mol. Med. 54(1): 51-60 [Abstract Only].
Ceballos et al, "Early alterations of plasma free amino acids in chronic renal failure", (1990) Clin. Chim. Acta 188(2): 101-108 [Abstract Only].
Chen et al, "In vivo renal arginine release is impaired throughout development of chronic kidney disease", (2010) Am. J. Physiol. Renal Physiol. 298(1): F95-F102.
Cobo et al, "Glutamine levels predict renal failure in patients treated with cisplatinum", (2007) Nefrologia. 27(1): 23-29.
Dumont et al, "Supplementation with a low dose of L-arginine reduces blood pressure and endothelin-1 production in hypertensive uraemic rats", (2001) Nephrol Dial Transplan. 16(4): 746-754.
Elliott et al, "Feline chronic renal failure: clinical findings in 80 cases diagnosed between 1992 and 1995", (1998) J. Small Anim. Pract. 39: 78-85.

(Continued)

*Primary Examiner* — Robert A Wax
*Assistant Examiner* — Olga V Tcherkasskaya
(74) *Attorney, Agent, or Firm* — Loza & Loza, LLP; Michael F. Fedrick

(57) ABSTRACT

A method of treating chronic kidney disease by administering to a subject a composition that includes L-arginine, glycine, L-glutamine, L-histidine, L-aspartic acid L-glutamic acid, and L-carnosine.

15 Claims, 9 Drawing Sheets

(56) References Cited

OTHER PUBLICATIONS

Elliott et al, "Acid-base balance of cats with chronic renal failure: effect of deterioration in renal function", (2003) J. Small Anim. Pract. 44(6): 261-268.

Fraser et al, "Short-Term Biological Variation of Plasma Analytes in Renal Disease", (1983) Clin. Chem. 29/3, 508-510.

Goldstein et al, :Plasma amino acid profiles in cats with naturally acquired chronic renal failure, (1999) Am. J. Vet. Res. 60(1): 109-113 [Abstract Only].

Henney et al. eds.,"Taste and Flavor Roles of Sodium in Foods: A Unique Challenge to Reducing Sodium Intake", Strategies to Reduce Sodium Intake in the United States, National Academies Press, 2010, pp. 1-12.

Heymsfield et al, "Measurement of muscle mass in humans: validity o the 24-hour urinary creatinine method", Am. J Clin. Nutr. Mar. 1983; 37: 478-494.

Ito-Kato et al, "Effect of carnosine on runt-related transcription factor-2/core binding factor alpha-1 and Sox9 expressions of human periodontal ligament cells", (2004) J. Periodontal Res. 39(3): 199-204.

Kopple et al, "Evidence that histidine is an essential amino acid in normal and chronically uremic man", (1975) J. Clin. Invest. 55(5): 881-891.

Kumar et al, "Serum amino acid profile in chronic renal failure", (1998) Indian J. Nephr. 8(2): 52-54.

Lulich, "Feline renal failure: questions, answers, questions", Feb. 1992, Natl Agricultural Library, v 14 (2).

Mitch et al, "Creatinine metabolism in chronic renal failure", (1980) Clin. Sci. 58(4): 327-335.

Mitch et al, "The effect of a keto acid-amino acid supplement to a restricted diet on the progression of chronic renal failure", (1984) N. Engl. J. Med. 311(10): 623-629.

Moncada et al, "Nitric oxide: physiology, pathophysiology, and pharmacology", (1991) Pharmacol. Rev. 43(2): 109-142.

Morris et al, "Arginine: an essential amino acid for the cat", (1978) J. Nutr. 108(12): 1944•1953.

Nissim et al, "Glycine attenuates Fanconi syndrome induced by maleate or ifosfamide in rats", (1996) Kidney Int. 49(3): 684-695.

Pan et al, "Cytoprotection by glycine against ATP-depletion-induced injury is mediated by glycine receptor in renal cells", (2005) Biochem. J. 390(Pt 2): 447-453.

Perriello et al, "Regulation of gluconeogenesis by glutamine in normal postabsorptive humans", (1997) Am. J. Physiol. 272(3 Pt 1): E437-445.

Reyes et al, "Role of arginine in health and in renal disease", (1994) Am. J. Physiol. 267(3 Pt 2): F331-F346.

Rogers et al, "Essentiality of amino acids for the growing kitten", (1979) J. Nutr. 109: 718-723.

Smoyer et al, Enhanced GFR response to oral versus intravenous arginine administration in normal adults:, (1991) J. Lab. Clin. Med. 118(2):166•175.

Stumvoll et al, "Human kidney and liver gluconeogenesis: evidence for organ substrate selectivity", (1998) Am. J. Physiol. 274 (Endocrinol. Metab. 37): E817-E826.

Stumvoll, "The human kidney as an important producer of glucose", May 1998, Med Klin (Munich) 15:93(5):300-6.

Suliman et al, "Inflammation contributes to low plasma amino acid concentrations in patients with chronic kidney disease", (2005) Am. J. Clin. Nutr. 82(2): 342-349.

Syme et al, "Survival of Cats with Naturally Occurring Chronic Renal Failure Is Related to Severity of Proteinuria", J Vet Intern Med 2006;20:528-535.

Tada et al, "Toxic effects of L-aspartic acid at high dose levels on kidneys and salivary glands in Fischer 344 rats detected in a 90-day feeding study", (2008) Food Chem. Toxicol. 46(8): 2789•2795.

Tizianello et al, "Renal metabolism of amino acids and ammonia in subjects with normal renal function and in patients with chronic renal insufficiency", (1980) J. Clin. Invest. 65(5): 1162-1173.

Watanabe et al, "Consequences of low plasma histidine in chronic kidney disease patients: associations with inflammation, oxidative stress, and mortality", (2008) Am. J. Clin. Nutr. 87: 1860-1866.

Wernerman, "Clinical use of glutamine supplementation", (2008) J. Nutr. 138(10): 2040S-2044S.

Wu et al, "The effect of glutamine on protein turnover in chick skeletal muscle in vitro", (1990) Biochem. J. 265(2): 593-598.

Xu et al, "BMP-7 counteracts TGFbetal-induced epithelial-to mesenchymal transition in human renal proximal tubular epithelial cells", (2009) J. Nephrol. 22(3): 403•410.

Yatzidis, "Oral supplement of six selective amino acids arrest progression renal failure in uremic patients", (2004) Int. Urol. Nephrol. 36(4): 591-598.

Yin et al, "Protective effect of glycine on renal injury induced by ischemia-reperfusion in vivo", (2002) Am. J. Physiol. Renal Physiol. 282(3): F417-F423.

Zeisberg et al, "BMP-7 counteracts TGF-beta1-induced epithelial-to-mesenchymal transition and reverses chronic renal injury", (2003) Nt. Med. 9(7): 964-968.

Zeisberg et al, "Bone morphogenic protein-7 induces mesenchymal to epithelial transition in adult renal fibroblasts and facilitates regeneration of injured kidney", (2005) J Biol Chem, 280(9):8094-8100.

International Search Report and Written Opinion for PCT/US13/73732 dated Mar. 6, 2014; 8 pages.

"Renavast promotes healthy kidney function," www.renavast.com, Oct. 11, 2011; 1 page.

Declaration of Mark Garrison, dated Nov. 17, 2015; 2 pages.

Extended European Search Report for European Patent Application No. 13861349.2 dated Apr. 18, 2016; 8 pages.

Yatzidis, Hippocrates "Oral supplement of six selective amino acids arrest progression renal failure in uremic patients", Intl Urology and Nephrology, DO, vol. 36 No. 4, Dec. 1, 2004, pp. 591-598, XP019269710, ISSN: 1573-2584.

* cited by examiner

TREATMENT FOR CHRONIC KIDNEY DISEASE

CROSS-REFERENCE TO RELATED APPLICATIONS

This application is the U.S. national stage of International Patent Application No. PCT/US2013/073732, filed on Dec. 6, 2013 and entitled TREATMENT FOR CHRONIC KIDNEY DISEASE, which claims the benefit of priority under 35 U.S.C. §120 from U.S. Patent Application No. 61/734,080, filed on Dec. 6, 2012 and titled "TREATMENT FOR CHRONIC RENAL FAILURE," and from U.S. patent application Ser. No. 13/892,225, filed on May 10, 2013 and titled TREATMENT FOR CHRONIC KIDNEY DISEASE. The disclosures of the foregoing applications are incorporated herein by reference in their entirety.

BACKGROUND

Chronic kidney disease (CKD), also known as chronic renal disease or chronic renal failure, is a progressive loss in renal function over a period of months or years. CKD can be caused by a variety of conditions and mechanisms, and affects both humans and other mammals, in particular cats. Renal function in geriatric cats progressively declines over time, leading to end-stage disease.

Different approaches to preventing the progression of renal disease have been attempted, including protein-restricted diets, the control of hypertension with angiotensin converting enzyme (ACE) inhibitors, diet substitution of saturated fats with polyunsaturated fats, and treatment with immunosuppressants such as mycophenolate mofetil (MME), corticosteroids such as prednisone, and morphogenic agents such as bone morphogenic protein-7 (BMP-7). None of these treatments have reliably stopped or reversed disease progression, though some experiments with BMP-7 have shown promise. There remains a need, therefore, for better treatments for chronic kidney disease.

FIGURES

SUMMARY

Figure 1:
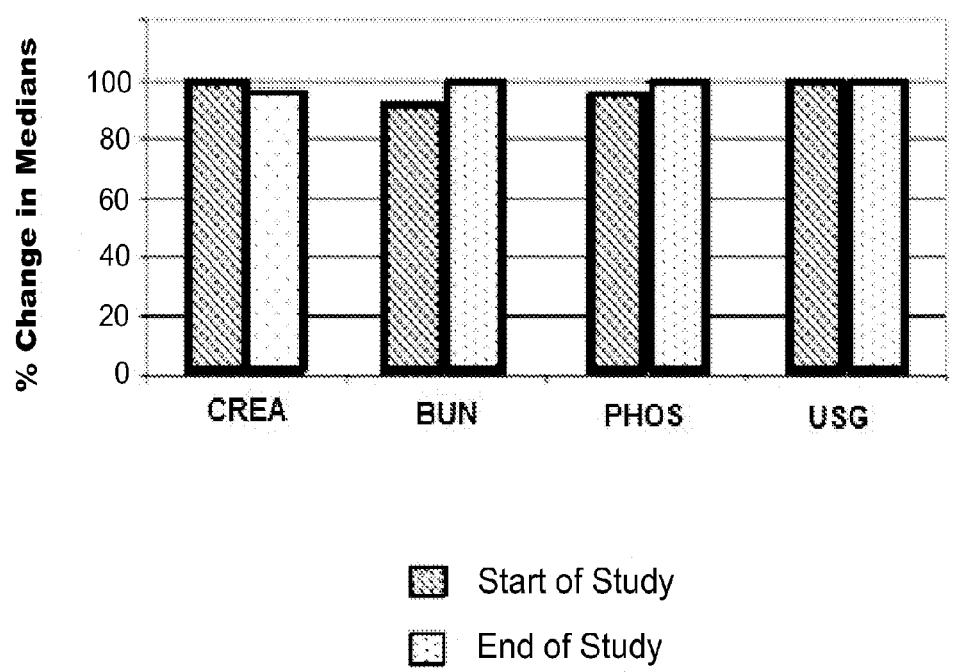
FIG. 1 is a chart showing the percentage change in median values of blood-serum concentrations of creatinine (CREA), phosphate (PHOS), blood urea nitrogen (BUN) and urine specific gravity (USG) in a study of cats treated with the present composition.
Figure 2:
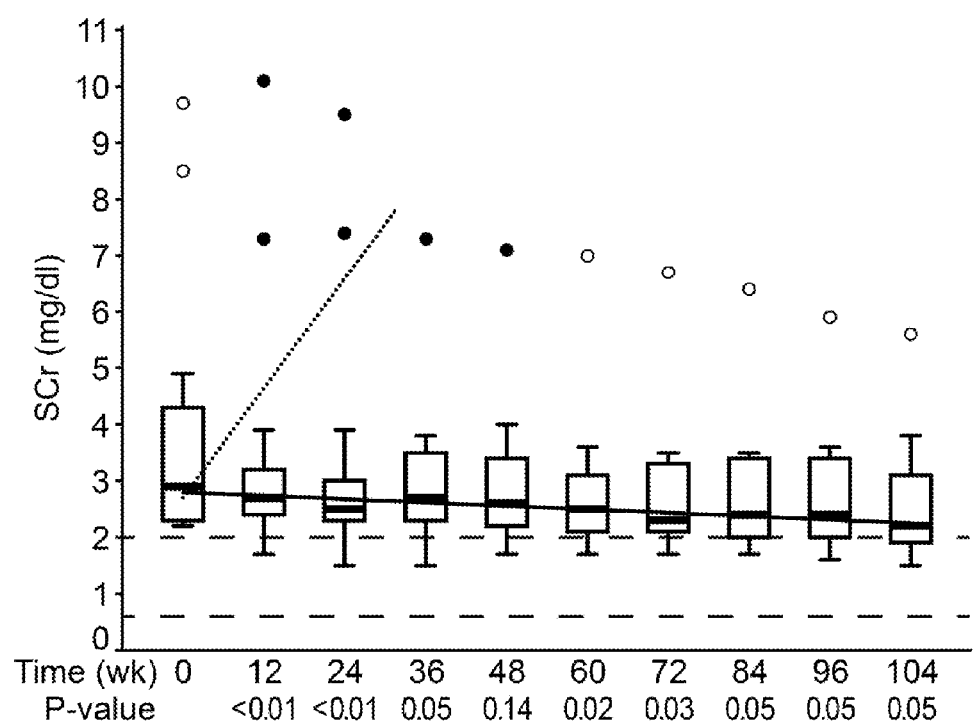
FIG. 2 is a chart showing creatinine (CREA) levels in a study of cats treated with the present composition.
Figure 3:
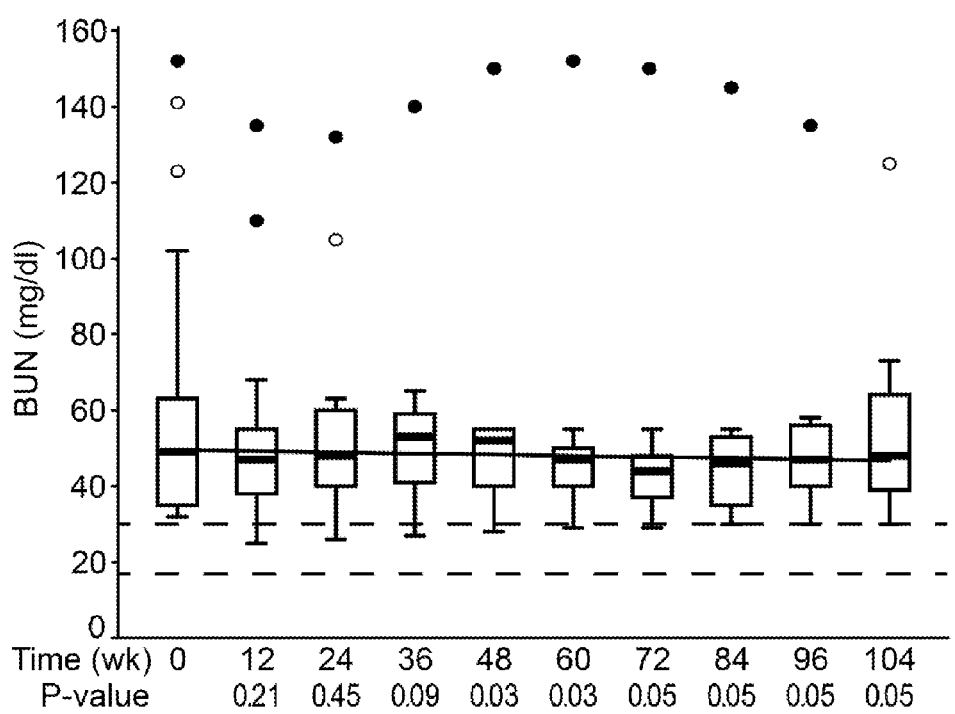
FIG. 3 is a chart showing phosphate (PHOS) levels in a study of cats treated with the present composition.
Figure 4:
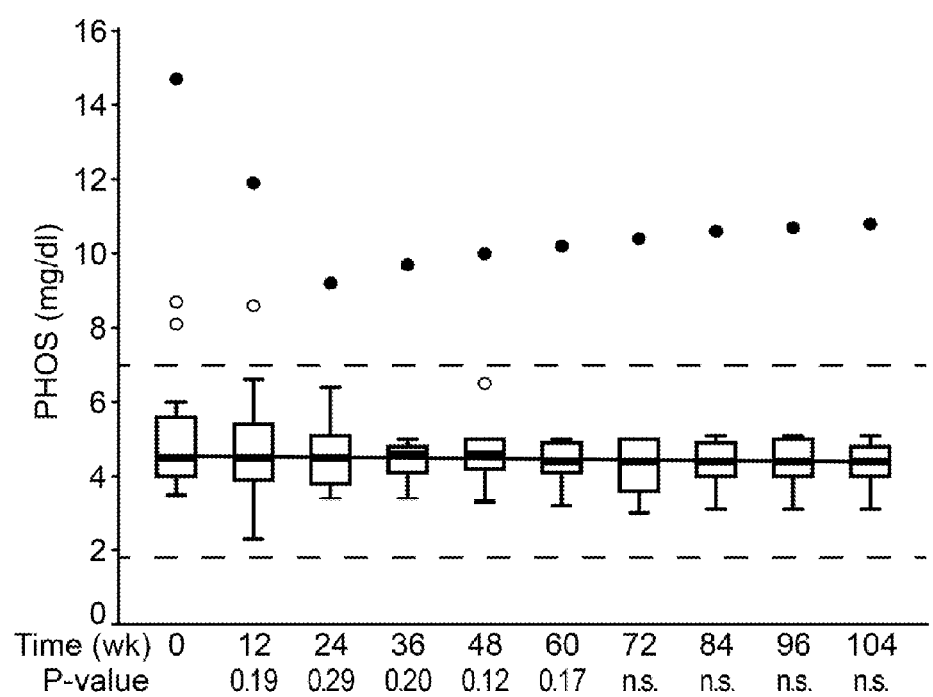
FIG. 4 is a chart showing blood urea nitrogen (BUN) levels in a study of cats treated with the present composition.
Figure 5:
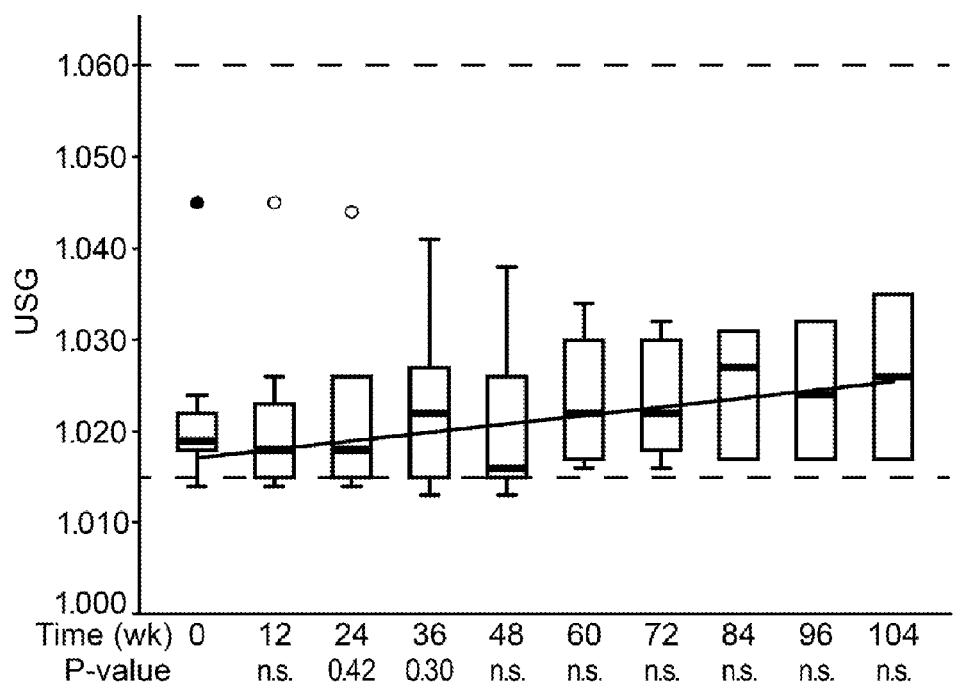
FIG. 5 is a chart showing urine specific gravity (USG) levels in a study of cats treated with the present composition.

Chronic kidney disease can be treated with the present composition, which comprises L-arginine, glycine, L-glutamine, L-histidine, L-aspartic acid, L-glutamic acid, and L-carnosine, or a salt of one or more of the foregoing which is suitable for enteral administration. Preferably, the composition comprises:

between 8% and 30% by weight glycine, preferably between 15% and 20%;
 between 8% and 30% by weight L-aspartic acid, preferably between 15% and 20%;
 between 8% and 30% by weight L-glutamic acid, preferably between 15% and 20%;
 between 8% and 30% by weight L-glutamine, preferably between 15% and 20%;
 between 3% and 15% by weight L-histidine, preferably between 5% and 10%;
 between 3% and 15% by weight L-arginine, preferably between 5% and 10%; and
 between 8% and 30% by weight L-carnosine, preferably between 15% and 20%.

The foregoing percentages are based on the combined weight of the L-arginine, glycine, L-glutamine, L-histidine, L-aspartic acid, L-glutamic acid, and L-carnosine in the composition. The L-glutamic acid in the formulation is preferably provided in a form in which 90% or more of the granules have a particle size of 40 microns (0.040 mm) or less, for example 44 microns (0.044 mm) or less. The L-glutamic acid is also preferably provided as monosodium glutamate.

In another embodiment, a 300 milligram portion of the present composition comprises:

between 25 mg and 100 mg glycine;
 between 25 mg and 100 mg L-aspartic acid;
 between 25 mg and 100 mg L-glutamic acid;
 between 25 mg and 100 mg L-glutamine;
 between 10 mg and 50 mg L-histidine;
 between 10 mg and 50 mg L-arginine; and
 between 25 mg and 100 mg L-carnosine, The composition can be formulated in a variety of ways, for example as either a liquid or solid. In liquid form, the composition can be formed as a solution, a dispersion, a suspension, or an emulsion. In solid form, present as a powder, granules, a tablet, or a gel, for example, and can be encapsulated. In some embodiments the L-aspartic acid can be in the form of aspartic acid monosodium salt monohydrate.

The foregoing composition can also be used to treat chronic kidney disease in a subject, preferably in a mammal such as a cat, dog, or human. In this regard, the composition can be used in a method of treating chronic kidney disease in which the composition is administered to such a subject. The composition can be advantageously administered in an amount of between 50 mg/kg and 200 mg/kg, based on the weight of the L-arginine, glycine, L-glutamine, L-histidine, L-aspartic acid, L-glutamic acid, and L-carnosine in the composition to the weight of the subject. The composition can be administered either once or twice daily, for example, and is preferably administered enterally, and more preferably orally.

Before administering the present composition, the subject should be tested to determine whether the subject has or is at risk of developing CKD. If the subject does not have chronic kidney disease but is at risk of developing CKD, the subject can be treated prophylactically with the present composition. If the subject is determined to have chronic kidney disease, then treatment with the present composition is indicated. The subject can be determined to have chronic kidney disease for example when the subject's glomerular filtration rate over a surface area of 1.73 m² is 89 or less, and in particular when the subject's glomerular filtration rate is 29 or less. A creatinine level of over 2.2 mg/dL can also be used as an indicator that the subject has CKD.

DESCRIPTION

Definitions

As used herein, the following terms and variations thereof have the meanings given below, unless a different meaning is clearly intended by the context in which such term is used.

"About" and "approximately," when used in reference to a numerical value means plus or minus ten percent of the indicated value, quantity, or amount. For example and not by way of limitation, "about 10" means between 9 and 11, and "about 10%" means between 9% and 11%, unless the context indicates otherwise. More preferably "about" and "approximately," indicates a value within 3%, 2%, or 1% of the indicated value.

"BUN" and "blood urea nitrogen" refer to the amount of nitrogen in a blood sample that comes from urea. Elevated levels of BUN, for example >20 mg/dL, and more particularly above 50 mg/dL, are associated with CKD.

"Chronic kidney disease" and "CKD" refer to a progressive loss in renal function by a subject.

"CREA" refers to creatinine and/or to the level (amount) of creatinine in a sample, usually of blood or serum. A CREA level of 2.2 mg/dL is generally indicative of CKD. Creatinine is a chemical waste product in the blood that passes through the kidneys to be filtered and eliminated in urine.

"Enteral" refers to a route of administration of a composition that involves absorption of the composition through the gastrointestinal tract. Enteral administration includes administration of a composition in solid, liquid, gel, or other form via the mouth and/or esophagus, for example orally, buccally, or through a feeding tube such as a nasogastric or nasojejunal feeding tube. Enteral administration also includes administration via a surgically inserted gastric tube or rectal administration such as with a suppository.

"Granule" and "particle" refer to a single continuous piece of a solid substance.

"Mesh" refers to the number of openings (of relatively uniform size) per linear inch (25.4 mm) in a sieve, and/or to the size of particles able to pass through such openings. When referencing particle size, mesh describes a material in which 90% or more of the material will pass through the openings of a sieve having the stated number of openings per linear inch (25.4 mm), i.e. in which 90% or more of the particles comprising the material are approximately the same size as or are smaller than the size of the opening.

"Particle" and "granule" refer to a single continuous piece of a solid substance. "Particulate" refers to a composition composed of or comprising particles.

"PHOS" refers to phosphate and/or to the level (amount) of phosphate in a sample, usually of blood or serum. Elevated levels of phosphate, for example >3.5 mg/dL, such as 6-7 mg/dL, are associated with CKD.

"Subject" refers to a mammal in need of treatment for CKD, including humans and animals, e.g., companion animals (dogs, cats, ferrets and the like), farm animals (cows, sheep, pigs, horses, and the like), non-domesticated mammals (tigers, lions, apes, chimpanzees and the like), and laboratory animals (rats, mice, and guinea pigs and the like).

"Treatment" includes both prophylactic treatment before a subject experiences a decline in renal function and also the treatment of CKD after a subject experiences a decline in renal function.

"USG" refers to urine specific gravity, i.e. the specific gravity of a urine sample from a subject. Decreased USG, e.g. a specific gravity of less than 1.035, can be an indicator of CKD.

"VAS" or "Visual Analogue Scale" is a measurement technique for measuring a characteristic, such as hunger or pain that ranges across a continuum of values. Values corresponding to the magnitude of the characteristic as experienced by a subject are recorded by the subject at particular points in time in studies which make use of a VAS.

The term "comprise" and variations of the term, such as "comprising" and "comprises," are not intended to exclude other additives, components, integers or steps. The terms "a," "an," and "the" and similar referents used herein are to be construed to cover both the singular and the plural unless their usage in context indicates otherwise.

Unless otherwise distinguished herein, references to amino acids and peptides, such as L-arginine, glycine, L-glutamine, L-histidine, L-aspartic acid, L-carnosine, and L-glutamic acid, include enterally acceptable salts and similar derivatives of such amino acids and peptides.

Composition

The present composition comprises amino acids and a peptide, in particular the amino acids L-arginine, glycine, L-glutamine, L-histidine, L-aspartic acid, L-glutamic acid and the dipeptide L-carnosine (beta-alanyl-L-histidine). Without being limited to a particular theory, the amino acids L-arginine, glycine, L-glutamine, L-histidine, L-aspartic acid and L-glutamic acid are believed to have beneficial effects which increase the glomerular filtration rate, reduce inflammation, act as cytoprotective agents, and increase nitric oxide production of a subject when taken enterally, while L-carnosine is believed to increases the production of BMP-7, a morphogenic protein belonging to the transforming growth-factor superfamily. L-arginine, for example, is believed to protect renal tissue from the negative effects of renal ischemia and facilitate the disposal of protein and metabolic waste. Glycine is believed to exert a cytoprotective effect against a variety of cellular insults, as well as increasing GFR and thereby improving kidney function. L-glutamine, L-aspartic acid, L-glutamic acid and L-histidine are scavengers of reactive oxygen species, and histidine is also believed to have anti-inflammatory properties. L-carnosine is believed to increase the production of BMP-7, which has been found to experimentally induce mesenchymal-to-epithelial transition in renal fibroblasts and therefore to facilitate the regeneration of injured kidneys. The synergistic effect of these amino acids and dipeptide on the treatment of CKD, however, was not previously known.

Representative quantities of the components of the present composition are shown in Table 1 below, which lists preferred weight percentages of these components (not including other excipients included in a particular embodiment of the composition):

TABLE 1

| Components | Concentration Range (wt. %)* | Preferred Range (wt. %)* |
|---|---|---|
| Glycine | 8-30 | 15-20 |
| L-Aspartic acid | 8-30 | 15-20 |
| L-Glutamic acid | 8-30 | 15-20 |

TABLE 1-continued

| Components | Concentration Range (wt. %)* | Preferred Range (wt. %)* |
|---|---|---|
| L-Glutamine | 12-30 | 15-20 |
| L-Histidine | 3-15 | 5-10 |
| L-Arginine | 3-15 | 5-10 |
| L-Carnosine | 8-30 | 15-20 |

*The totals for any particular embodiment of the present composition would equal 100%.

In one embodiment, the present composition can comprise the foregoing components in the amounts shown in Table 2 below, for a 300 mg dosage (exclusive of other formulation excipients):

TABLE 2

| Component | Range | Preferred Range |
|---|---|---|
| Glycine | 25-100 mg | 50-75 mg |
| L-Aspartic acid | 25-100 mg | 50-75 mg |
| L-Glutamic acid | 25-100 mg | 50-75 mg |
| L-Glutamine | 25-100 mg | 50-75 mg |
| L-Histidine | 10-50 mg | 25-35 mg |
| L-Arginine | 10-50 mg | 25-35 mg |
| L-Carnosine | 25-100 mg | 50-75 mg |

The components of the composition are preferably provided in a water soluble form, for example as a sodium or potassium salt, so that the composition can be dissolved and provided in liquid form. Aspartic acid and glutamic acid, for example, can be provided in the form of a sodium salt (e.g., aspartic acid monosodium salt monohydrate and/or monosodium glutamate). Aspartic acid has a solubility of only about 4 g/L, for example, while its sodium salt has a solubility of ≥100 g/L. It is preferred that the active components of the present composition be provided in a form which dissolves quickly, both for purposes of liquid formulation and in order to increase the bioavailability of the components when provided in solid form, in order to avoid a delay in their absorption in a subject's gastrointestinal tract. Therefore, providing these components in the form of a salt, in particular a soluble salt such as a sodium or potassium salt, when possible, is preferred. Those of skill in the art of formulation are able to select appropriate pharmaceutically or nutritionally suitable salts of the components of the present composition.

The particle size of at least one of the components of the present formulation, L-glutamic acid, preferably provided in the form of monosodium glutamate (MSG), has surprisingly been found to influence the palatability of the present composition and thus the feeding compliance of subjects, i.e. the likelihood that the present composition will be consumed (when administered orally). Subjects fed the present composition exhibit a significant preference for formulations which contain glutamic acid provided in particle sizes of 0.040 mm (40 microns) or less, corresponding to about 320 mesh, as compared to formulation which contain glutamic acid provided in larger particle sizes, such as sizes of between 0.177 mm and 0.250 mm (177-250 microns), corresponding to between 60 and 80 mesh. The glutamic acid component of the present composition is therefore preferably provided in particle sizes of about 320 mesh or smaller, i.e. 0.040 mm or less, such as in sizes of 325 mesh (0.044 mm or 44 microns) or smaller. Due to manufacturing tolerances, it is to be understood that a component which is specified to be of a certain size falls within this parameter when 90% or more of the particles comprising the component are of the specified size or are within the specified parameter. It is also understood that due to the manner in which particles of the present composition are manufactured and/or sorted (such as through sieving), particles of a specified size will generally be of that size or smaller.

The composition can be provided in a variety of ways known to the art. Compositions for oral use or for enteral administration by another route include solid dosage forms such as, e.g., powders, granules, tablets, capsules, and lozenges. The composition can also be provided in fluid or liquid formulations such as, e.g. solutions, suspensions (aqueous or non-aqueous), emulsions, colloidal dispersions, gels, and other mixtures. Such dosage forms can be formulated using dietary and/or pharmaceutically acceptable excipients and additives known to those of skill in the art, such as preservatives, colorants, flavoring agents, plasticizers, humectants, and buffering agents. With respect to solid dosage forms, such excipients can include, for example, inert diluents or fillers, such as sucrose, sorbitol, sugar, mannitol, microcrystalline cellulose, starches including potato starch, calcium carbonate, sodium chloride, lactose, calcium phosphate, calcium sulfate, or sodium phosphate; granulating and disintegrating agents, for example, cellulose derivatives including microcrystalline cellulose, starches including potato starch, croscarmellose sodium, alginates, or alginic acid and chitosans; binding agents, for example, maltodextrin, sucrose, glucose, sorbitol, acacia, alginic acid, sodium alginate, gelatin, starch, pregelatinized starch, microcrystalline cellulose, magnesium aluminum silicate, sodium carboxymethylcellulose, methylcellulose, hydroxypropyl methylcellulose, ethylcellulose, polyvinylpyrrolidone, polyvinylacetate, or polyethylene glycol; and chitosans; and lubricating agents, for example, magnesium stearate, zinc stearate, stearic acid, silicas such as silicon dioxide, hydrogenated vegetable oils, or talc.

When the composition is in the form of a tablet or a capsule filled with the present composition, the tablet or a capsule can be coated e.g. with a sugar coating, a film coating (e.g. based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g. based on methacrylic acid copolymer, cellulose acetate phthalate, hydroxypropyl methylcellulose phthalate, hydroxypropyl methylcellulose acetate succinate, polyvinyl acetate phthalate, and/or ethylcellulose). The capsules can be soft or hard gelatin capsules, in which the composition can be present in granular or powder form.

The present composition is advantageously formulated as a pharmaceutical and/or veterinary composition. Excipients approved for use in pharmaceutical formulations and/or veterinary formulations can therefore be combined with the present composition in order to form an appropriate pharmaceutical and/or veterinary composition.

Treatment of CKD

The present composition can be used to treat CKD, both prophylactically and after a subject experiences a decline in renal function. A subject found to be at risk for CKD, based on risk factors such as age and/or due to other symptoms or medical conditions known to be associated with CKD, can be administered the present composition prophylactically in order to prevent or slow the onset of CKD. Alternatively or in addition, a subject can be treated after CKD has been diagnosed in the subject. Subjects treated for CKD with the present composition are generally mammals, in particular dogs, cats, and/or humans.

The severity of CKD is generally classified into five stages in humans and four stages in dogs and cats, all of which can be treated with the present composition. CKD is associated with several diagnostic markers, with glomerular filtration rate (GFR) generally considered to be an accurate diagnostic marker of CKD. Levels below 90 milliliters per minute (the beginning of stage 2 CKD) indicate decreased kidney function and thus the onset of CKD. The stages of CKD, as measured by GFR, are shown in Table 3 below:

TABLE 3

Stages of CKD

| Stage | Glomerular Filtration Rate (GFR, ml/min.)* | Description |
| --- | --- | --- |
| 1 | 90+ | Normal kidney function |
| 2 | 60-89 | Mildly reduced kidney function |
| 3 | 30-59 | Moderately reduced kidney function |
| 4 | 15-29 | Severely reduced kidney function |
| 5 | <15 | End stage renal disease (ESRD) |

*GFR values are normalized to an average surface area (size) of 1.73 m².

GFR can be calculated in ways known to the art, such as by measuring the renal clearance of an exogenous marker that is freely filtered by the kidney and does not undergo metabolism, tubular secretion or absorption, such as inulin. CKD is also associated with other diagnostic markers, including CREA, BUN and PHOS and USG. CKD is a progressive disease that results in statistically significant increases in blood-serum concentrations of CREA, BUN and PHOS, and lowered USG over time. Creatinine levels over about 2.0 mg/dL, preferably over 2.2 mg/dL, and more preferably over 2. 2.3 mg/dL can be used as an indication of CKD in a subject. Likewise, BUN levels of over 60 mg/dL, increased phosphate levels (e.g., over about 6 mg/dL), and USG levels of <1.035 can indicate that a subject has CKD.

Prior to administering the present composition, a subject is preferably tested to determine one or more of the GFR, CREA, BUN, PHOS, and/or USG of the subject in order to determine whether the subject has CKD. If the subject is determined to have CKD, the present composition can then be administered to the subject in order to halt or attenuate the progression of renal failure, and in some cases reverse the disease.

The present composition is preferably administered enterally. Generally, the composition will be eaten or consumed as a liquid by the subject, i.e. taken orally via the mouth and/or esophagus, and can be taken in admixture with food or also without food. Other forms of enteral administration are also possible. For example, the composition can be administered buccally or sublingually in an appropriate formulation. Preferably, the present composition is administered in amounts of between 50 mg/kg and 500 mg/kg per day (with respect to the components of the composition listed in Tables 1 and 2 above), and more preferably in amounts of between 100 mg/kg and 200 mg/kg per day. A preferred dose of the composition listed in Tables 1 and 2 is 300 milligrams, but doses of between 10 mg and 1,000 mg, more preferably between 200 mg and 600 mg, can also advantageously be administered. Administration of the composition is preferably accomplished once or twice per day, but other intervals are also possible.

EXAMPLES

Example 1

Effect on Feline Renal Function

Nineteen cats with chronic kidney disease were treated with the present composition for periods ranging up to two years. Cats were confirmed as having CKD (1) if their blood-serum CREA concentration was equal to or greater than the mean of the Stage II value-range of the International Renal Interest Society classification of stages of renal disease, (2) if their USG was less than 1.035, (3) if their BUN concentration was elevated near or above the high end of the normal range, (4) if their PHOS was elevated near or above the high end of the normal range, and (5) if their clinical history included signs attributable to CKD (i.e. persistent azotemia, chronic polyuria and polydipsia, or small kidneys on abdominal palpitation). If one or more of these signs were present with increased CREA (i.e., if serum CREA concentration was equal to or greater than the mean of the Stage II value-range of the International Renal Interest Society classification of stages of renal disease (2.2 mg/dL)), the cat was considered for inclusion in the study. The criteria used to establish the cessation of progressive renal injury were (1) a halt in the rise of blood-serum concentrations of CREA, BUN, and PHOS and a halt to the decline of USG, all for an extended period of time. No statistically significant deterioration in these values would signify no statistically significant disease progression. Cat owners were given informed consent forms for review and acceptance. The amino acids and peptide in the present composition were purchased from Spectrum Chemical Company (Gardena, Calif.).

The subjects, ranging in weight from 2.8 Kg to 5.5 Kg, all on non-protein-restricted commercial diets, received two 300-mg oral daily doses of the present composition as a dietary supplement. The composition included approximately 50 mg glycine (17 wt %), 50 mg L-aspartic acid (17 wt %), 50 mg L-glutamic acid (17 wt %), 50 mg L-glutamine (17 wt %), 50 mg L-carnosine (17 wt %), 25 mg L-histidine (8 wt %), and 25 mg L-arginine (8 wt %), with the aspartic acid being present as either L-aspartic acid or L-aspartic acid monosodium salt monohydrate. Doses were either mixed with 1.5 milliliters of water and administered directly into each subject's mouth, or were sprinkled directly on a small amount of food and fed to the subject. The present composition was readily accepted without rejection. Blood serum concentrations of CREA, BUN, PHOS and USG measurements were made for each subject at varying intervals during the twenty four month study (mean=13 months, median=15 months, range=3-24 months).

Figure 6:
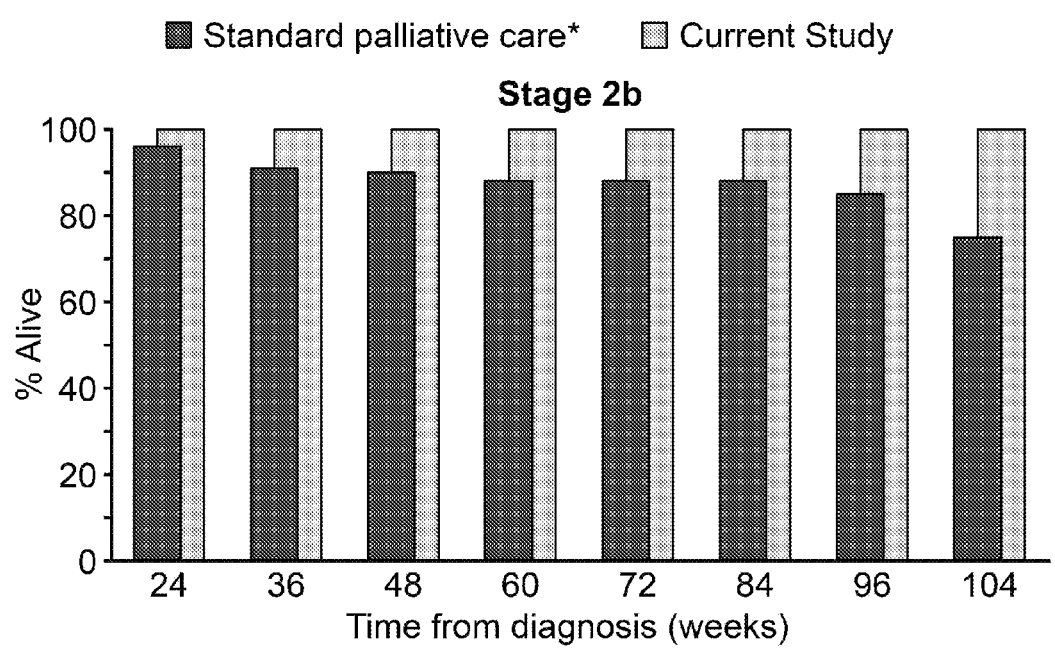
FIG. 6 is a chart showing the survival rate of cats with stage 2 b CKD which were treated with the present composition.
Figure 7:
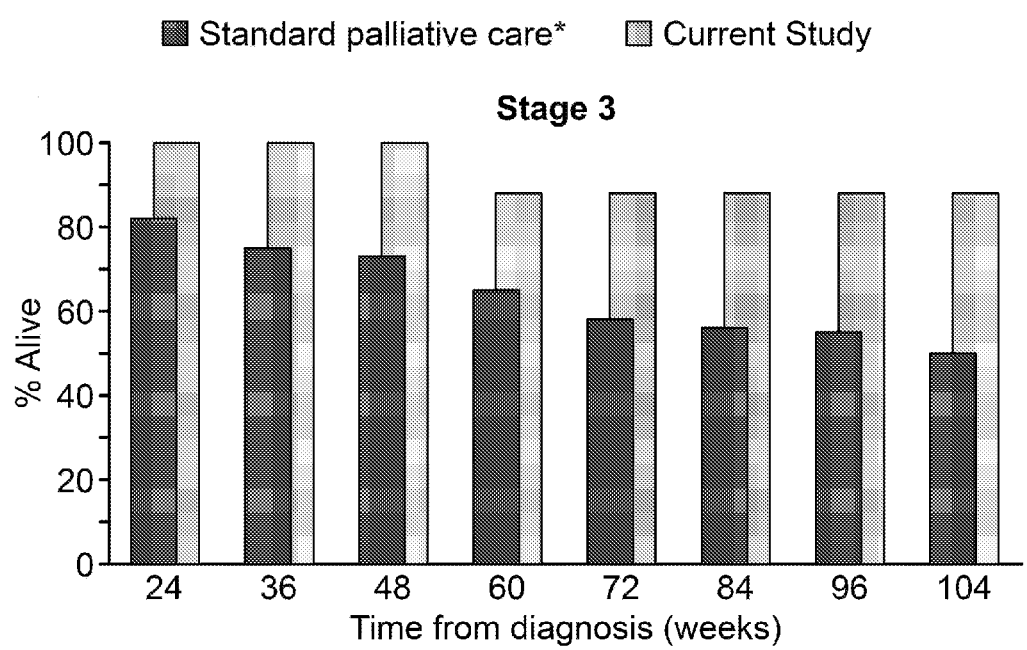
FIG. 7 is a chart showing the survival rate of cats with stage 3 CKD which were treated with the present composition.
Figure 8:
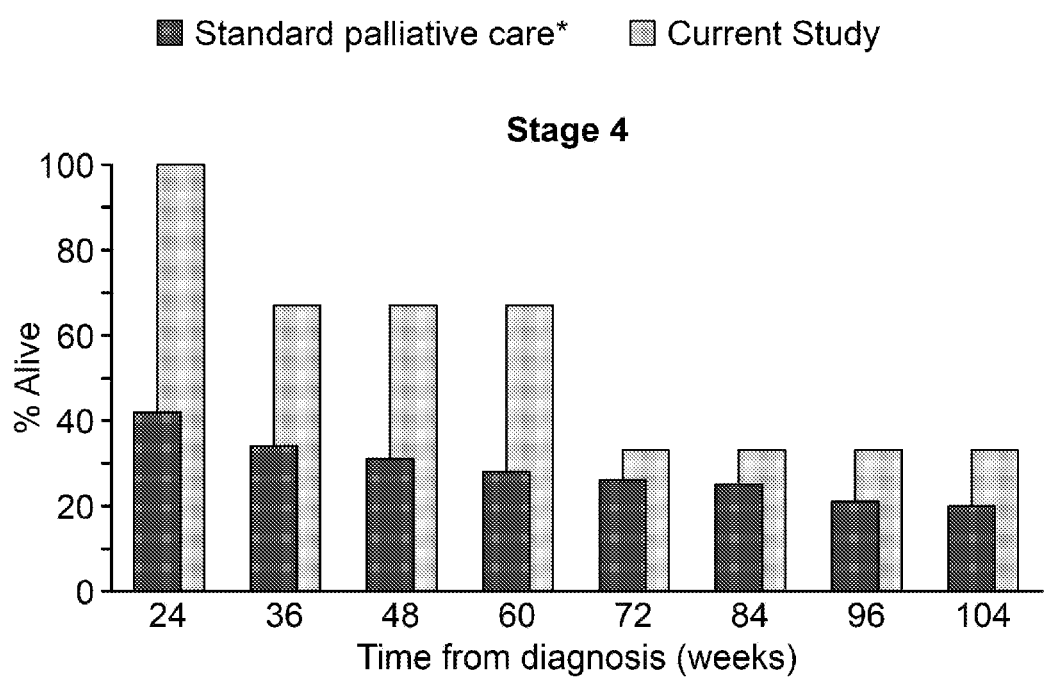
FIG. 8 is a chart showing the survival rate of cats with stage 4 CKD which were treated with the present composition.

The typical decline of renal function reported in geriatric cats with CKD receiving standard palliative care, as measured by increases in CREA, BUN, PHOS and lowered USG was not observed in the sample population. As seen in FIGS. 1-5, CREA decreased significantly in the cohort of cats over eight of the nine measurement intervals (approximately every twelve weeks) (Median, mean P=0.05, 0.04). Median BUN declined significantly over the last six intervals (Median, mean P=0.05a, 0.04). Median PHOS and USG were not significantly changed. Survival of all cats in all disease stages was enhanced when compared to prior reports of survival of cats receiving standard palliative care (P=0.01, 0.01, 0.01), as can be seen from FIGS. 6-8. The present composition halted the deterioration of measured blood-serum biochemical parameters in the majority of cats with chronic kidney disease. These findings suggest that the present composition can be a valuable tool in treating and halting the progression of chronic kidney disease.

Each subject was monitored over the course of the study. Assessments were made for general body condition, weight change and ease of administration of the present composition. There were no owner complaints or concerns regarding administration of the supplement and many cats regarded direct oral administration (i.e., not mixed in food) as a treat. There was a statistically significant decrease in CREA mean values for all test periods (i.e. week 0 through week 104), with the exception of one period only. BUN also showed a general statistically significant stabilization. PHOS and USG showed no statistically significant change (i.e. stabilization).

The typical decline of renal function reported in geriatric cats with CKD was not observed for the entire two-year treatment period in 89.4% of cats treated with the present composition. General body condition, including coat, appearance and grooming habits, improved in each subject during the study, and most gained weight. There were no reports of gastrointestinal upset or diarrhea. FIG. 1 shows the percentage change in median values, while FIGS. 2-5 show the CREA, BUN, PHOS, and USG values measured over the course of the study.

Example 2

Effect of MSG Particle Size on Feeding Compliance

The effect of the particle size of the glutamic acid component of the present composition was investigated in order to determine whether this affected subjects' ingestion of the composition. Feline subjects were fed two variants of a composition having the following active ingredients: glycine (17 wt %), L-aspartic acid (17 wt %), L-glutamic acid (17 wt %), L-glutamine (17 wt %), L-carnosine (17 wt %), L-histidine (8 wt %), and L-arginine (8 wt %). In one of the variants, the L-glutamic acid component (provided as monosodium glutamate, MSG) was ground to a particle size of between 60 and 80 mesh (0.177 mm-0.250 mm), while in the other variant the MSG component was ground to a particle size of 320 mesh (0.040 mm).

A total of seventeen cats were fed a standardized diet consisting of Friskies Ocean White Fish and Tuna for 14 days. The elapsed time for the total consumption of this diet was recorded for each feeding and the median total-consumption time was calculated. Following this, the same group of cats was then fed for 14 days with the same standardized diet, but in addition including 300 mg of the composition described above sprinkled evenly on top of the food. This composition included MSG (50 milligrams) ground to a particle size of 320 mesh. Median consumption times were calculated. After this, the same group of cats was fed for a further 14 days with the standardized diet and 300 mg of the composition sprinkled evenly on top of the food, with the MSG (50 milligrams) now present in a particle size of between 60 and 80 mesh. Median consumption times were likewise calculated.

Figure 9:
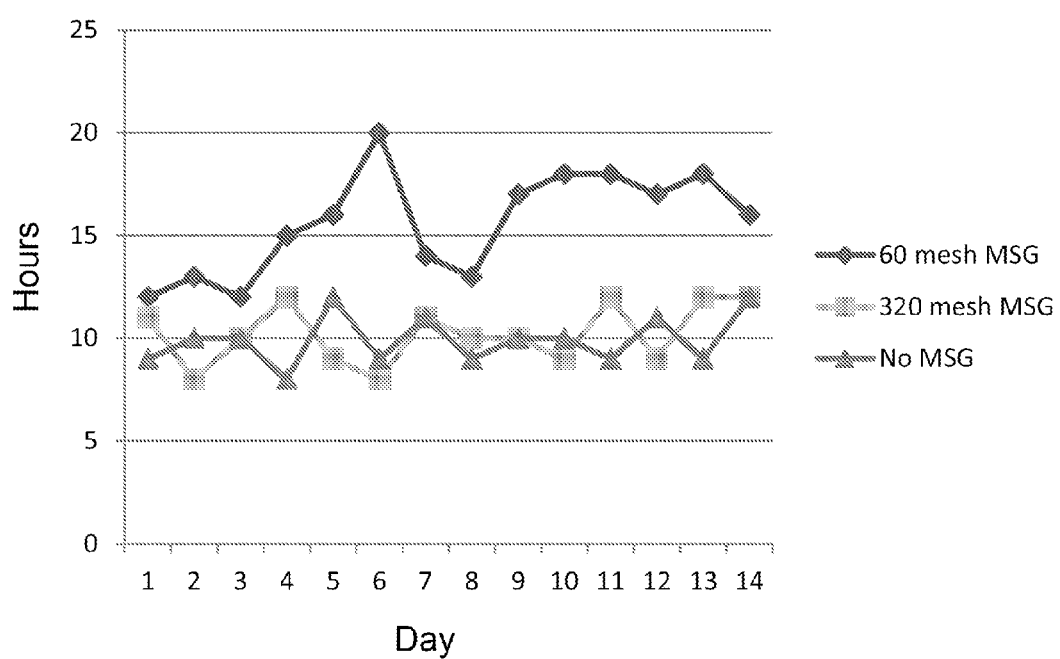
FIG. 9 is a graph showing the average consumption by cats of different food formulations.

The results of this experiment are shown in FIG. 9. As can be seen in the chart in this figure, there was no significant difference in the median consumption times between the standardized diet alone and the standardized diet having the composition with 320 mesh MSG (P=0.59). However, the median consumption time of the standardized diet with the composition having 60-80 mesh MSG was significantly lengthened (P=0.001). The size of the MSG particles in the composition thus significantly influenced the palatability of the composition, and also thus the level of feeding compliance, with larger sized MSG particles decreasing palatability.

Example 3

Effect of MSG Particle Size on Palatability

A human subject ingested an amount of two compositions having the following active ingredients: glycine (17 wt %), L-aspartic acid (17 wt %), L-glutamic acid (17 wt %), L-glutamine (17 wt %), L-carnosine (17 wt %), L-histidine (8 wt %), and L-arginine (8 wt %). In one of the compositions, the monosodium glutamate (MSG) component was ground to a particle size of between 60 and 80 mesh (0.177 mm-0.250 mm), while in the other composition the MSG component was ground to a particle size of 320 mesh (0.040 mm).

The subject tasted a quantity of each of the two compositions. Using a scale of 1 to 10 in the manner of a visual analog scale, with 10 being most palatable, the subject ranked the composition having MSG particles sized at 60-80 mesh as a 4. The subject ranked the composition having MSG particles sized at 320 mesh MSG as an 8.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure.

Recitation of value ranges herein is merely intended to serve as a shorthand method for referring individually to each separate value falling within the range. Unless otherwise indicated herein, each individual value is incorporated into the specification as if it were individually recited herein. All references and patent applications cited herein are incorporated by reference in their entirety.

What is claimed is:

1. A composition suitable for enteral administration for use in treating chronic kidney disease in mammals, wherein the composition consists of:
   between 8% and 30% by weight glycine;
   between 8% and 30% by weight L-aspartic acid and/or salts thereof;
   between 8% and 30% by weight L-glutamic acid and/or salts thereof;
   between 8% and 30% by weight L-glutamine;
   between 3% and 15% by weight L-histidine;
   between 3% and 15% by weight L-arginine; and
   between 8% and 30% by weight L-carnosine,
   based on the total weight of composition,
   wherein the L-glutamic acid and/or salts thereof is present in a particulate form having a particle size of less than or equal to 320 mesh.

2. The composition of claim 1, wherein the composition consists of:
   between 15% and 20% by weight glycine;
   between 15% and 20% by weight L-aspartic acid;
   between 15% and 20% by weight L-glutamic acid;
   between 15% and 20% by weight L-glutamine;
   between 5% and 10% by weight L-histidine;
   between 5% and 10% by weight L-arginine; and
   between 15% and 20% by weight L-carnosine,
   based on the total weight of the composition.

3. The composition of claim 1, wherein the salt of L-glutamic acid is monosodium glutamate.

4. The composition of claim 1, wherein the salt of L-aspartic acid is aspartic acid monosodium salt monohydrate.

5. The composition of claim 1, wherein the composition is present in a solid form selected from the group consisting of a powder, granules, a tablet, and a gel.

6. The composition of claim 1, wherein the composition is present in a liquid form selected from the group consisting of a solution, a dispersion, a suspension, and an emulsion.

7. The composition of claim 1, wherein the composition is formulated for oral administration.

8. The composition of claim 1, wherein the composition is formulated for veterinary use.

9. A method of treating chronic kidney disease in a mammalian subject in need thereof, wherein the subject is a cat or a dog, comprising the step of administering the composition of claim 1 to the subject.

10. The method of claim 9, wherein the composition is administered enterally.

11. The method of claim 9, wherein the composition is administered once or twice daily in an amount of from 50 mg and 200 mg per kilogram of the subject weight.

12. The method of claim 9, wherein the subject is a dog.

13. The method of claim 9, wherein treatment is performed after a subject experiences a decline in renal function.

14. The method of claim 12, wherein the subject is a cat.

15. The method of claim 9, wherein the composition is present in a solid form selected from the group consisting of a powder, granules, and a tablet.

\* \* \* \* \*